United States Patent [19]

Revici

[11] Patent Number: 4,565,690
[45] Date of Patent: Jan. 21, 1986

[54] METHOD FOR TREATING DRUG ADDICTION

[75] Inventor: Emanuel Revici, New York, N.Y.

[73] Assignee: Elena Avram, New York, N.Y.

[21] Appl. No.: 722,493

[22] Filed: Apr. 12, 1985

[51] Int. Cl.⁴ .................. A61K 31/21; A61K 31/095; A61K 31/105; A61K 31/265; A61K 31/045; A61K 33/04
[52] U.S. Cl. ...................................... 424/10; 424/162; 514/512; 514/513; 514/706; 514/707; 514/724; 514/738; 514/812
[58] Field of Search ................. 424/10, 162; 514/512, 514/513, 706, 707, 724, 738, 810, 812, 813

[56] References Cited

U.S. PATENT DOCUMENTS

| 3,622,676 | 11/1971 | D'Alonzo | 424/162 |
| 4,346,082 | 8/1982 | Revici | 424/192 |
| 4,416,869 | 11/1983 | Revici | 424/164 |
| 4,512,977 | 4/1985 | Lundy | 424/162 |

Primary Examiner—Stanley J. Friedman
Attorney, Agent, or Firm—Pennie & Edmonds

[57] ABSTRACT

A method for treating drug addiction from compounds which cause a catabolic effect on the human body, which comprises administering to said body, a sufficient amount of an anabolic agent containing bivalent negative selenium or sulfur.

16 Claims, No Drawings

METHOD FOR TREATING DRUG ADDICTION

TECHNICAL FIELD

The invention relates to methods and compositions for treating drug addiction, particularly for the treatment of the symptoms of withdrawal when the patient terminates using drugs.

BACKGROUND ART

In treating patients for drug addiction, the most common method employed is that of allowing the patient to "dry out" or eliminate the drug from their system. This period, called withdrawal, is a very difficult time for the patient, since the body is in need of the drug due to its previous habitual use and dependence thereon.

It was previously not recognized that the effect of the drug on the body would be counteracted by administering a compound which produces an opposite effect on the body so as to offset and neutralize the detrimental defense effects of the body. The present invention provides one such solution for this problem.

SUMMARY OF THE INVENTION

The invention relates to a method for treating drug addiction from compounds which cause a catabolic fatty acids defense effect on the human body, which comprises administering to said body, a sufficient amount of antifatty acids agents, preferred antifatty acid agents includes a variety of agents comprised of selenium and sulfur compounds. The active ingredient of these agents can be administered orally or by injection. Preferred dosages include about 10 ml of the oil (about 0.5 to 1 gram).%

The invention also relates to a method for treating drug addiction from compounds which cause a catabolic noxious effect on the human body, which comprises admistering to said body, a sufficient amount of antifatty acid agents.

DETAILED DESCRIPTION OF THE PREFERRED EMBODIMENTS

My study concerning drug addiction and the symptoms of withdrawal is based on the recognition of a dualism, in the pathogenisis of the condition and the action of such agents on the human body. This dualism is shown in the antagonistics of the anabolic-constructive and catabolic-destructive conditions, of such agents. In the pathogenesis of the anabolic condition, abnormal sterols intervene while in the pathogenisis of the catabolic condition, abnormal fatty acids having as characteristic the presence of trienic conjugated formations intervene. Clinically, these catabolic conditions are observed as insomnia, diarrhea, vomiting, cramps, generalized are localized pair, particularly in the bones and joints, horiplations and tremors in the patent. The stronger the catabolic condition of the drug agent the more intensive the clinic manifestations.

In order to determine whether the agents are either anabolic or catabolic in effect, an entire series of tests must be conducted. In the test of pH of second day wound crust, an anabolic agent induces a lower pH, while a catabolic agent produces a higher pH. In the study of the curve of healing wounds, an anabolic agent makes any peaks disappear, while the catabolic agent increases a leukocytosis, eosinophilia, a lowering of the serum potassium and more free water, while the catabolic agent causes directly opposite changes. In higher specific gravity, a lowering of the chlorides and of calcium excretion.

By applying this research to the problem of any addiction it was found that the agents which induce an addiction have typical anabolic characters, and their action induces a typical anabolic imbalance.

By applying the influence exerted by these various agents upon the oxygen uptake of cancer cells, suspension or yeast, using the YST oxygen monitor, it was found that, over a period of time, the anabolic agents reduced the uptake of oxygen, while the catabolic agents increased it. However, for the anabolic agents, their initial action caused an increase in the oxygen uptake was taking place. This paradoxical action was induced in fact by the action of low amounts of the active agent. This paradoxical action seen in the oxygen uptake test also explains the clinical action with two phases for the addictive drugs studied. The first phase corresponds to a cerebral excitration, followed by the second, of deep sleep, corresponding to a typical anabolic action. This is seen for the narcotics with a primary excitation, followed by deep sleep.

The recognition of the typical anabolic character for the addicting drugs, represents the first fundamental discovery for the treatment of this problem.

In a study of body defenses, I found that the body defends itself against an anabolic agent which is repeatedly introduced, by manufacturing antagonistic lipids having a catabolic character—i.e., fatty acids. The abnormal nature of these fatty acids is due to the presence of trienic conjugated formations. The defense character of these fatty acids appears in two ways. First, in their relationship with the anabolic drug, which corresponds to a reciprocal neutralization whereby the fatty acids neutralize the anabolic drug, while the anabolic drug neutralizes the noxious action of the abnormal fatty acids. Also, due to its defense character, the body has a tendency to increase its manufacture of the necessary neutralization agents. Due to this reciprocal neutralization, the presence of an excess of the defensive fatty acids requires the need for the drug in order to neutralize it. The more drugs introduced, the more fatty acids are manufactured in a defense action; the more fatty acids are present, the more need for the drug to neutralize them. This explains the two manifest characters of addiction, the appearance of the need for the drug, and the progressive increase of this need.

In withdrawal, the high amount of the catabolic defense fatty acids remains in the body, since they do not have the anabolic drug to neutralize them. It is the presence of these fatty acids which induce the manifestations of withdrawal. The symptoms are typically catabolic as occur due to the action of the abnormal fatty acids; i.e., insomnia, diarrhea, vomiting, cramps, perspiration, pain in the bones, and horipilations. Dienic and trienic conjugated formations are found through spectral analysis present in the urines. Analytical data of blood and urine show the presence of such catabolic conditions. The presence of an urinary strong alkalosis indicates the presence of this catabolic imbalance directly affecting the systemic level.

The recognition of a catabolic imbalance, due to the presence of high amounts of noncompensated abnormal fatty acids, constitutes the main character of the drug withdrawal condition. An action upon these fatty acids represents the consequent therapeutic intervention.

Numerous means to act upon these abnormal trienic conjugated fatty acids have now been discovered. In one, an oxidation of the abnormal fatty acids was considered. In the study of the actions upon such fatty acids, it appears interesting to note their oxidating change under specific conditions. Several specific characters have been found to effect this change. In one, the agent has a lipidic character. This appeared to be effective due to the affinity between lipids and the primary character of the fatty acids which are lipids.

The action of selenium was also found to work well when used in the bivalent negative state. I found a fundamental difference between bivalent negative and tetra and hexavalent positive selenium. The bivalent negative selenium has an oxidation character similar to that of the minus 2 of oxygen, and has different effectiveness than the tetra or hexavalent positive oxidation states.

Furthermore, preparations having bivalent negative selenium and lipidic characters are preferred. For this aim, a method for introducing these elements into unsaturated fatty acids was developed.

By heating an oil, such as an unsaturated fatty acid or a mixture of them, at a critical temperature, the double bonds open. At this place, therefor, an element can be attached. For a bivalent negative selenium the result of this attachment of one atom corresponds to an epoxy, while two atoms correspond to a peroxy, depending upon the exact temperatures used.

According to the invention, a mixture of a vegetable oil and gray or red selenium is heated until the selenium is incorporated. This occurs around 215° C., when the solution becomes clear. Polyunsatured vegetable oils have been found to be the most advantageous for use in the invention.

A preferred polyunsatured vegetable oil is sesame seed oil, although any naturally occurring vegetable, animal or fish oil can be utilized. Alternately, the same mixture can be heated to above 240° C. until foaming has ceased. Either of these two preparations can be used separately or preferably mixed together. The preferred route of administration is by intramuscular injection. These preparation whether used separately or in combination, have been shown to possess an extemely low toxicity in both animals and humans.

In very severe cases of withdrawal, from methadone for example, a number of doses of from 0.5 to 1 gram % selenium in this oil were injected per day, and this without any subjective or objective side effects. In general, much lower doses are preferred in order to induce an efficient detoxification. The doses are indicated by the clinical response of the patient, and they may be increased if any withdrawal symptoms remain. It is preferable to prevent any withdrawal symptoms from occurring in the patient.

The changes in the patient were evident in the blood analyses. The original withdrawal symptoms were unusually controlled by a single injection of about 10 ml, the effect is being seen within 45 minutes. A treatment of several days is necessary to obtain a good detoxification which would continue as long as the subject did not again take the addicting drugs.

Members of the following groups of agents represent other compositions to treat or intervene in the treatment of drug withdrawal by acting upon these abnormal fatty acids. They may be used alone or preferably in combination with the selenium-oil mixture. The agents are lipoidal in character, i.e., they are more soluble in neutral solvents than in water so that they act directly upon the fatty acids.

Such groups include: selenium as a bivalent negative liposoluble compounds, such as organic selenides and selenium incorporated in fatty acids; sulfur as colloidal sulfur; crystals from sulfurized or selenized oil; thiosulfates; thioglycerols; thioglycols; ethylene trithio carbonate; organic lipidic bivalent negative sulfides, disulfides, mercaptans; lipidic compounds or incorporated in oils or fatty acids; lipsoluble ethers, preferably butyl ether and butyl-oxy-phenyl ether; fatty alcohols and also these obtained as mixtures, by treating the fatty acids of animal or vegetable oils with lithium-aluminum-hydride.

Sterols obtained especially as unsaponifiable fractions from fats, oils, organs, organism or other biological material, i.e., more soluble in neutral solvents than in water. Other groups are the lipidic alcohols, i.e., those which are more soluble in neutral solvents than in water, such as pentanol, heptanol, 3-pentanol and 3-heptanol, pentyl and heptylamines and especially 3-heptylamine. Lipidic aminoalcohols, liposoluble epoxide and peroxides; the anabolic elements of the 1A, 111 A, VA, V11 A, 11 B, 1V B, V1 B, and iron and nickel series, and liposoluble corticoids are also useful according to the invention. With adequate or sufficient amounts, favorable action was obtained with members of each group.

It has appeared advantageous to use combinations of members of more than one group, and this reduced the inherent side effects of each agent. Most advantageously, these combinations should be used together with the selenium incorporated in oil.

The clinical applications show the need to have the treatment continued for several days after all the symptoms of withdrawal have fully disappeared. This is done in order to control the natural body tendency to continue to manufacture the abnormal fatty acids as a defensive action.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for treating drug addiction in a human body from compounds which have caused the body to produce abnormal fatty acids having a catabolic character which comprises administering to said body a sufficient amount of an antifatty acid agent comprising a lipidic or liposoluble organic compound containing bivalent negative selenium or sulfur to counteract the effects of said abnormal fatty acids.

2. The method of claim 1 wherein the agent is an organic selenide; selenium incorporated in a fatty acid; crystals from sulfurized or selenized oil; a thisolufate; an organic lipidic sulfide, disulfide, or mercaptan; a thioglycerol; or a thioglycol.

3. The method of claim 1 wherein the active ingredient is administered by injection.

4. The method of claim 1 wherein the active ingredient is administered orally.

5. A method for treating drug addiction in a human body from compounds which have caused the body to produce abnormal fatty acids having a catabolic character which comprises administering to said body a sufficient amount of an antifatty agent comprising the reaction product produced by heating at least one animal, vegetable, or fish oil and elemental selenium at a temperature between about 215° and 240° C. for a sufficient time to incorporate at least 0.1% selenium into the oil, to counteract the effects of said abnormal fatty acids.

6. The method of claim 5 wherein about 10 ml of the oil composition is administered orally to a body.

7. The method of claim 5 wherein between about 0.5 to 1 gram % of oil in injected into said body.

8. The method of claim 5 wherein the composition further comprises liposoluble alcohols, amines, 3-alcohols, 3-amines or molecules with odd number of carbon fatty alcohols.

9. The method of claim 1 wherein the composition further comprises liposoluble epoxides or peroxides.

10. The method of claim 5 wherein the composition further comprises liposoluble epoxides or peroxides.

11. A method for treating drug addiction in human body from compounds which have caused the body to produce abnormal fatty acids having a catabolic character which comprises administering to said body a sufficient amount of an antifatty acid agent comprising colloidal sulfur or ethylene trithio carbonate to counteract the effects of said abnormal fatty acids.

12. The methods of claim 11 wherein the agent is administered by intramuscular injection.

13. The method of claim 11 wherein the agent further comprises an organic selenide; crystals from sulfurized or selenized oil; an organic lipid sulfide, disulfide, or mercaptan; a thiosulfate; a thioglycol; or a thioglycerol.

14. The method of claim 11 wherein the agent further comprises liposoluble alcohols, amines, 3-alcohols, 3-amines, or molecules with odd number of carbon fatty alcohols.

15. The method of claim 5 wherein the agent further comprises an organic selenide; crystals from sulfurized or selenized oil; an organic lipid sulfide, disulfide, or mercaptan; a thiosulfate; a thioglycol; or a thioglycerol.

16. The method of claim 11 wherein the agent further comprises at least one liposoluble epoxide or peroxide.

* * * * *